(12) United States Patent
Rump (10) Patent No.: US 10,500,400 B2
(45) Date of Patent: Dec. 10, 2019

(54) ELECTRODE LEAD, IMPLANT, AND METHOD FOR IDENTIFYING AN ELECTRODE LEAD

(71) Applicant: BIOTRONIK SE & Co. KG, Berlin (DE)

(72) Inventor: Jens Rump, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 218 days.

(21) Appl. No.: 15/667,680

(22) Filed: Aug. 3, 2017

(65) Prior Publication Data
US 2018/0050214 A1 Feb. 22, 2018

(30) Foreign Application Priority Data

Aug. 16, 2016 (EP) ..................................... 16184297
Aug. 16, 2016 (EP) ..................................... 16184298
Aug. 16, 2016 (EP) ..................................... 16184299

(51) Int. Cl.
*A61N 1/372* (2006.01)
*A61N 1/04* (2006.01)
(Continued)

(52) U.S. Cl.
CPC .......... *A61N 1/37229* (2013.01); *A61B 90/98* (2016.02); *A61N 1/025* (2013.01);
(Continued)

(58) Field of Classification Search
CPC ........ A61N 1/37229; A61N 1/05; A61N 1/37; A61N 1/025; A61N 1/3752; A61N 1/08;
(Continued)

(56) References Cited

U.S. PATENT DOCUMENTS 5,720,293 A 2/1998 Quinn et al.
5,755,742 A 5/1998 Schuelke et al.
(Continued)

FOREIGN PATENT DOCUMENTS

DE 10 2008 040 867 12/2009
WO 2011093875 A1 8/2011

OTHER PUBLICATIONS

European Search Report and Annex to the European Search Report on European Patent Application No. EP 16 18 4299.2, dated Dec. 5, 2016 (7 pages).
(Continued)

*Primary Examiner* — Gary D Harris
(74) *Attorney, Agent, or Firm* — Buchanan Ingersoll & Rooney PC (57) ABSTRACT

An electrode lead having a plug for connecting to an implant having a control device and a communication antenna connected to the control device, and having at least one electrical conductor and one insulating tube insulating the at least one electrical conductor. To simply/reliably transmit information of the electrode lead to the implant (with a low expenditure of energy), a hermetically sealed passive RFID label is embedded: in the insulating tube, and/or in the plug, or in an insulating body of a separate additional part connectable to the insulating tube or the plug. The RFID label has an RFID chip and an inlay antenna connected in an electrically conducting manner to the RFID chip. The inlay antenna is electromagnetically coupled to the at least one electrical conductor and the communication antenna. A corresponding method for identifying an electrode lead and a corresponding implant are also contemplated.

3 Claims, 4 Drawing Sheets

(51) Int. Cl.
*A61N 1/08* (2006.01)
*A61N 1/375* (2006.01)
*A61B 90/98* (2016.01)
*A61N 1/02* (2006.01)
*A61N 1/37* (2006.01)
*A61N 1/05* (2006.01)
*G01R 19/25* (2006.01)

(52) U.S. Cl.
CPC .............. *A61N 1/0488* (2013.01); *A61N 1/05* (2013.01); *A61N 1/08* (2013.01); *A61N 1/37* (2013.01); *A61N 1/3752* (2013.01); *A61N 1/04* (2013.01); *G01R 19/2503* (2013.01)

(58) Field of Classification Search
CPC ........ A61N 1/0488; A61N 1/04; A61B 90/98; G01R 19/25
USPC ......................................................... 429/151
See application file for complete search history.

(56) References Cited

U.S. PATENT DOCUMENTS

| | | | |
|---|---|---|---|
| 7,713,194 | B2 | 5/2010 | Zdeblick |
| 7,983,763 | B2 | 7/2011 | Stevenson et al. |
| 2003/0018369 | A1 | 1/2003 | Thompson et al. |
| 2004/0073265 | A1 | 4/2004 | Scheiner |
| 2006/0212083 | A1 | 9/2006 | Scheiner |
| 2006/0212096 | A1 | 9/2006 | Stevenson |
| 2007/0203547 | A1* | 8/2007 | Costello ................. A61N 1/056 607/59 |
| 2008/0065181 | A1 | 3/2008 | Stevenson |
| 2011/0112609 | A1 | 5/2011 | Peterson |
| 2012/0123496 | A1 | 5/2012 | Schotzko et al. |
| 2014/0330347 | A1 | 11/2014 | Simms, Jr. |
| 2014/0343633 | A1 | 11/2014 | Kaula et al. |

OTHER PUBLICATIONS

European Search Report and Annex to the European Search Report on European Patent Application No. EP 16 18 4298.4, dated Apr. 24, 2017 (5 pages).

European Search Report and Annex to the European Search Report on European Patent Application No. EP 16 18 4297.6, dated Feb. 2, 2017 (7 pages).

European Search Report and Annex to the European Search Report on European Patent Application No. EP 17 18 4616.5, dated Feb. 1, 2018 (7 pages).

* cited by examiner

ELECTRODE LEAD, IMPLANT, AND METHOD FOR IDENTIFYING AN ELECTRODE LEAD

CROSS-REFERENCE TO RELATED APPLICATIONS

This patent application claims the benefit of and priority to co-pending European Patent Application No. EP 16184299.2, filed on Aug. 16, 2016, European Patent Application No. EP 16184297.6, filed on Aug. 16, 2016, and European Patent Application No. EP 16184298.4, filed on Aug. 16, 2016, which are all hereby incorporated by reference in their entireties.

TECHNICAL FIELD

The present invention relates to an electrode lead for connecting to an implant by means of a plug having at least one electrical conductor and one insulating tube insulating the at least one electrical conductor, to a method for identifying an electrode lead, and to an implant having a socket for connecting to the plug of an electrode lead.

BACKGROUND

Implants (implantable medical devices, IMD) such as cardiac pacemakers, defibrillators, and neurological devices like deep brain stimulators for deep brain stimulation, spinal cord stimulators, TENS (transcutaneous electrical nerve stimulators), devices for muscular stimulation therapy, and diagnostic equipment that tests the chemical properties of the blood of the patient, other body parts, or other properties and parameters of the body, frequently use electrode leads that are guided into the patient's body and remain there for at least the treatment or measurement period. Electrode leads are connected to the implant in an electrically conducting manner.

The implants normally include a biocompatible housing having an associated electronic circuit and an energy supply, e.g., a battery. The housing has a socket to which one or a plurality of electrode leads may be connected, for example, by means of a plug. Electrode leads transmit the electrical energy or data from the housing to the part of the body being treated or examined or vice versa.

In the context of the present invention, the term "electrode lead" shall be construed to mean a lead having an electric conductor or a plurality of electric conductors together with the enclosing insulating tube, which electrically insulates the electrical conductors from the outside and one another, and all of the other functional elements that are securely connected to the lead. As a rule, at its distal end, the electrode lead also comprises a so-called electrode tip, by means of which the electrical energy is introduced from the conductor(s) into the tissue to be treated. Frequently, an electrode tip is provided with anchor elements or retaining structures with which the physical position of the transition point for the electrical energy into the tissue to be treated is kept constant. The electrode tip may be embodied as a recording electrode, stimulating electrode, or measuring electrode. In addition, as a rule the electrode lead has, for instance at its proximal end, a plug with which the electrode lead may be connected to an implant, wherein for this the plug is inserted into a corresponding socket in the implant. The plug has one or a plurality of connectors, wherein each connector is connected with precisely one electrical conductor of the electrode lead. Correspondingly, in the socket, one connector of the socket is provided for each connector of the electrode lead.

Frequently, a plurality of electrode leads are connected to modern implants, for instance a multichamber cardiac pacemaker. In this case, efforts are made to configure the electrode leads and their connectors as thin and small as possible. However, this makes it more difficult to provide the plugs and connectors with easily visible markings and to differentiate the electrode leads. Moreover, as the number of electrode leads increases, so does the risk that individual electrode leads will be confused and/or incorrectly attached. It is therefore desirable for an implant to detect which electrode leads are connected so that it may actuate them appropriately. In addition, for operating the implant it is helpful when the electrode leads and/or their properties are identifiable for the implant.

U.S. Publication No. 2004/0073265 describes a device that provides an opportunity to detect incorrectly connected coronary leads and/or incorrect connections to cardiac rhythm management devices. To this end, a voltage introducing device of a pacemaker generates a voltage pulse between an electrode that is connected to a lead of the pacemaker and a head or housing electrode of the pacemaker. The housing electrode transmits a connection signal. The electrode is used to measure a corresponding connection signal using the lead. A measuring module of the device also measures one or a plurality of properties of the corresponding connection signal, such as current strength, voltage, impedance, and/or its time delay (after outputting the voltage pulse). The signal properties may be influenced by one or a plurality of leads and/or by intervening tissue and fluids (for example, a heart, including one or more of its chambers) disposed therebetween. A comparison module of the pacemaker may then establish whether the lead is properly guided to a contact of the pacemaker, wherein one or a plurality of properties of the corresponding connection signal are compared to appropriate preselected ranges of values. For instance, a measured impedance may be compared to an expected impedance range. The device described in the document thus does not selectively identify the lead, but on the contrary tests whether, following excitation of the body by a voltage pulse of a housing electrode for the pacemaker, the corresponding comparison signal received via a lead has properties within a prespecified range. The properties of the corresponding comparison signal are also determined by the excited body tissue between the housing electrode of the pacemaker and the receiving electrode. Only gross deviations, like those that occur due to a non-connected or completely incorrect type of lead, may be traced back to the lead with certainty; smaller deviations may be caused by the body. The aforesaid device therefore cannot provide the reliable and intentional detection of and differentiation between electrode leads having similar properties.

U.S. Publication No. 2006/0212083 also discloses a similar device. In this document, as well, it is stressed that the signal properties are influenced by the leads and/or by the intervening tissue or fluid disposed therebetween.

U.S. Publication No. 2011/0112609 describes a system for spinal cord stimulation having at least one implantable stimulating lead. It comprises, in particular, a medical programming device and an implantable pulse generator that is connected to one or to a plurality of implantable stimulating leads, each of which have a plurality of electrodes. The stimulating lead has one or two lead bodies. The electrodes fit precisely into the epidural space in the spinal column. Since the tissue there is conductive, electrical measurements may be taken between the electrodes. A control circuit of the implantable pulse generator takes such electrical measurements so that the medical programming device can automatically identify the individual lead bodies that are connected to the implantable pulse generator. The electrical measurements of the control circuit for identifying the connected lead bodies are field potentials. The control circuit may also measure the impedance at each electrode in order to determine the coupling efficiency between each electrode and the tissue and to determine the error detection for the connection between the electrode and the analog output circuit for the implantable pulse generator. In the known system, it is a drawback that the identification is not performed using the implantable pulse generator itself, but instead using an additional medical programming device.

U.S. Publication No. 2012/0123496 has to do with connectivity detection and type identification of an implanted lead for an implantable medical device. The device has a processor that can determine the connection and the type of lead. First, a signal measuring module tests the connection of the leads in that it tests values of electrical parameters during a signal between at least two electrodes, especially the impedance. One or more leads may have active electronics integrated therein that include one or more modular circuits integrated therein, depending on whether the lead is unipolar or multipolar. Each of the modular circuits is able to control a plurality of electrodes of the lead and includes a circuit arrangement that is connected electrically to one or a plurality of electrodes of the lead. As such, each of the modular circuits of a lead acts as an interface between the implanted medical device and the electrodes to which the modular circuit is connected. For measuring the impedance, the processor of the device controls the modular circuit such that the latter supplies a voltage pulse between a first and a second electrode. The signal measuring module measures the resulting current and the processor derives the impedance from this. In another step, the processor sends a query signal along a first conductor of the lead in order to obtain a reply about a second lead from the modular circuits. Such a response from each modular circuit supplies the processor information about the modular circuit and the electrodes it controls. In another configuration step, the processor transmits a signal via the first lead. The configuration step includes that the active configuration of the modular circuit is programmed. Refer to U.S. Pat. No. 7,713,194 for lead embodiments and active electronics and the modular circuits used therein. According to this publication, the modular circuit is embodied such that it is controlled via a bus. U.S. Publication No. 2012/0123496 consequently describes that the additional interface electronics of the modular circuits may be detected and thus the electrode lead may be determined. It is a drawback of the known device that complex modular circuits having active electronics for controlling the electrodes must be implemented and programmed. Furthermore, the information relates only to the modular circuits and the electrodes connected thereto, but not the lead as a whole.

U.S. Publication No. 2003/0018369 depicts a method and a device for automatically detecting and configuring implantable medical leads. For this method, a first communication circuit that stores data, such as model number and serial number, technical information, and calibration data, is connected to the lead or integrated therein. It has a receiver and a transmitter for receiving data signals from an external source. Thus, it may be programmed with identification data, calibration data, and other data during production. The first communication circuit is embodied as a passive transponder, and, in addition to the receiver and transmitter, also has an energy coupler for supplying energy and a control circuit that is connected to a non-volatile memory. The control circuit delivers the lead information stored in the memory to the transmitter/receiver of the transponder, which transmits the data via RF or other communication. During implantation of the lead, or thereafter, the information may be transferred to a second communication circuit outside of the lead. The transferred data may be used for identifying the lead, may be recorded in a patient file, and may be transferred to a central memory for use by the health service provider. Using the transponder, the lead may be detected automatically and the data stored in the memory may be transferred directly and forwarded. In addition to a transmitter and receiver, however, the transponder also needs a separate energy supply, a control unit, and a programmable digital memory. Because of this, the overall structure of the lead is relatively complex and expensive.

U.S. Publication No. 2014/0343633 also represents an electrically identifiable electrode lead having an identification module that has at least one filter, a current converter, a communication circuit, a load circuit, and a memory unit, such as an EPROM, for storing an identification code. Before the implant is inserted, each lead is implanted and connected to the implantable pulse generator (or an external pulse generator) that then retrieves self-identifying data from the identification module and can transmit this information to an external device like the medical programmer. The identification module can store up to 32 bytes of data for this. This method is repeated for each lead that is implanted. The identification module uses two available contacts of the lead for connecting to the implantable pulse generator. As in the aforesaid document, a digital memory is also required for this known electrode lead and the structure of the identification module is similarly complex.

Known from U.S. Publication No. 2006/0212096, U.S. Publication No. 2008/0065181, and U.S. Pat. No. 7,983,763 are devices for identifying an implantable medical device and an implantable conductor system in which an RFID tag having an RFID chip is arranged in the insulation surrounding the conductor or in the header block of an implantable device. Furthermore, a read device is provided that can wirelessly retrieve the data stored in the RFID chip about the device, the conductor system, the manufacturer, and the patient. The retrievable information does not contain any information about the current arrangement and/or the connection to the current electrode, however. In addition, the solutions explained in these documents suffer from the drawback that a comparatively large amount of energy must be expended for querying the data from the implant and for activating the chip. Additional devices used for this represent a significant SAR load (SAR=specific absorption rate–a measure for the absorption of an electromagnetic field through the tissue) for the patient.

The present invention is directed toward overcoming one or more of the above-mentioned problems.

SUMMARY

An object of the present invention is therefore to create an electrode lead that may be reliably and uniquely identified, even with respect to its connection and arrangement, but is also simple in its structure, works in an energy-saving manner, and may be produced cost-effectively. An object is furthermore to provide a simple method for identifying an electrode lead, which method permits clear assignment of electrode lead information to a socket of the implant. An object is furthermore to create a corresponding implant.

At least the above object(s) is attained using an electrode lead having the features of claim 1.

At least the above object(s) is attained using an electrode lead having a plug for connecting to an implant that has a control device and a communication antenna connected to the control device.

According to the present invention, provided in the electrode lead is a hermetically sealed passive RFID label embedded:

in the insulating tube, and/or in the plug, or in an insulating body of a separate additional part that is connectable to the insulating tube or the plug, preferably in a positive fit, wherein the RFID label has an RFID inlay with an RFID chip and an inlay antenna connected in an electrically conducting manner to the RFID chip, wherein the inlay antenna is electromagnetically coupled to the at least one electrical conductor and the communication antenna.

Using the inventive electrode lead, it is possible to retrieve information relating to the electrode lead in a simple and cost-effective manner without influencing the therapeutic path of the electrode lead by galvanic coupling. According to the present invention, the communication antenna and the electric lead of the electrode device work as a bipolar antenna. This significantly reduces the power required for retrieving the information. This also reduces the SAR load of the patient. In addition, it is possible to query only RFID labels that are disposed in the immediate vicinity of the electrode lead so that the query/transmitted information of the electrode lead to the implant is highly specific. Moreover, in the inventive solution it is not necessary to turn off EMI protective capacitors integrated in the implant as a filter unit against electromagnetic interference (EMI=electromagnetic interference) during such a query of data of the attached electrode lead.

For operating the electrical conductor of the electrode lead attached to the implant and the communication antenna of the implant as a bipolar antenna, it is advantageous when the path difference of the phase between the electrical conductor of the electrode lead at the site of the RFID label and communication antenna is between 140° and 220°, more preferred is between 150° und 210°, more preferred is between 160° und 200°, more preferred is between 170° and 190°, and more preferred is 180°.

An RFID label comprises an RFID chip and RFID inlay, wherein the RFID chip is arranged on the RFID inlay. The RFID inlay comprises a substrate on which are arranged the inlay antenna, optionally devices for impedance adjustment, and conductors or conductor paths for contacting the RFID chip with the inlay antenna with the optional device(s) for impedance adjustment.

According to the present invention, the passive RFID label may be embedded either in the insulating tube and/or in the plug. Alternatively, a separate component, specifically a so-called additional part, may be provided and the passive RFID label may be embedded, hermetically sealed, in its insulating body. The additional part is preferably embodied connectable, for instance attachable, to the insulating tube or the plug in a positive fit. The insulating body of the RFID label may comprise, for example, the same material as the insulating tube or the plug. For instance, the RFID label may be embodied on the outside of the insulating tube by using an insulating sleeve, as an additional part, that surrounds the insulating tube and hermetically seals the RFID label. For this, the RFID label is arranged between insulating tube and insulating sleeve and/or in the insulating sleeve.

In one preferred exemplary embodiment, the RFID chip has a memory unit, which may preferably be written multiple times, for storing information transmitted via the antenna, for instance 512 bits of free text and 240 bits for the electronic product code (EPC). In addition, information prespecified at the factory may be stored in the memory unit. This information may also be transmitted to the implant via the antenna of the RFID label and via the electrical conductor of the electrode lead. The information stored in the memory may comprise, for instance: manufacturer, type of electrode lead, serial number, date of manufacture, authorized regions, authorized conditions, date of implantation, implantation compatibility, MRI compatibility, and the like. The memory may furthermore include safety mechanisms and safety information that safeguard or identify the integrity (for instance, if some of the data are lost) and/or the authenticity (for instance during manipulation) of the stored information.

According to the inventive solution, the RFID chip of the RFID label is read by the active implant by means of the communication antenna and by means of the electrical conductor of the electrode lead, which are operated together as a bipolar antenna. The electrical conductor thus has a dual function, specifically its primary task related to conducting electrical signals—stimulating and/or measuring electrical signals of the body in which the electrode lead is implanted—and the inventive (secondary) function as a component of the antenna. Because the antenna of the RFID label is arranged in the immediate vicinity of the electrical conductor, the electromagnetic coupling is good and adequate signal strength for retrieving the information transmitted herewith remains on the RFID label, even with a low expenditure of energy by active implant. Damping losses are low. The implanted electrode leads may, in particular, be read individually in a targeted manner, which permits the information of the electrical electrode lead to be allocated to the position of this electrode lead (for instance, atrial, ventricular). There is no galvanic coupling of RFID label, especially of the inlay antenna of the RFID label, and an electrical conductor of the electrode lead.

The energy that is wirelessly coupled into the antenna of the RFID label by means of the bipolar antenna is calculated such that when this energy is transmitted to a location in the tissue of the patient, the temperatures occurring because of this do not exceed a maximum of 47° C. (limit for electromagnetic radiation that may be emitted into the human body, see e.g.: DIN EN 62209-1:2007-03 or VDE 0848-209-1:2007-03). In addition, the amplitudes used are always lower than the limits for undesired stimulation in the frequency range being used for transmitting information (for instance, 840 MHz to 960 MHz). See ANSI/AAMI/ISO 14117/Ed.1 for the assessment of electromagnetic tolerance of implants for treating tachycardia or bradycardia, or of devices for cardiac resynchronization therapy.

In one preferred exemplary embodiment, the RFID chip has a memory unit, which may preferably be written multiple times, for storing information transmitted via the antenna, for instance, 512 bits of free text and 240 bits for the electronic product code (EPC). In addition, information prespecified at the factory may be stored in the memory unit. This information may also be transmitted to the implant via the antenna of the RFID label and the bipolar antenna, comprising the communication antenna and the electrical conductor of the electrode lead. The information stored in the memory may comprise, for instance: manufacturer, type of electrode lead, serial number, date of manufacture, authorized regions, authorized conditions, date of implantation, implantation compatibility, MRI compatibility, and the like. The memory may furthermore include safety mechanisms and safety information that safeguard or identify the integrity (for instance, if some of the data are lost) and/or the authenticity (for instance during manipulation) of the stored information.

It is furthermore advantageous that the antenna of the RFID label is embodied as a metal layer, arranged on a plastic film, that preferably has at least one metal from the group containing platinum, gold, platinum alloys, and gold alloys. Such an antenna is simple and cost-effective to realize. Moreover, such an antenna is simple to attach to the electrode lead.

In another embodiment, the RFID label is embodied such that the complex conjugated of the impedance of the RFID chip equals the impedance of the RFID inlay, wherein the RFID inlay comprises an inlay antenna and, optionally, a device for adjusting the impedance of the RFID inlay. It is furthermore advantageous when the inlay antenna of the RFID label is adapted to the structure of the electrical conductor of the electrode lead; for instance, the inlay antenna may be embodied elongated if the electrical conductor of the electrode lead is embodied as an elongated conductor, such as, for instance, an extension conductor, or the inlay antenna may be embodied, for instance, as a helix if the electrical conductor of the electrode lead is embodied, for instance, as a coil conductor, wherein the winding direction of the helical inlay antenna is preferably the same as the winding direction of the coil conductor.

In another embodiment, the at least one electrical conductor and/or the arrangement of the antenna of the RFID label is set up or designed such that a current or voltage antinode of the oscillation may be produced in a prespecified frequency range at the location of the electromagnetic coupling of the inlay antenna with the at least one electrical conductor. This permits an improvement in the magnetic or electrical coupling between the antenna of the RFID label and the electrical conductor acting as a component of the bipolar antenna. For this, the electrode lead may be configured favorably for oscillation either in terms of its dimensions and/or electrical parameters and/or the electrical conductor may be sealed off on the implant side, that is, provided with an impedance value such that the desired oscillation behavior occurs in the prespecified frequency range.

At least the aforesaid object(s) is furthermore attained using a method for identifying an electrode lead described in the foregoing by means of an implant having a control device and a communication antenna connected to the control device, wherein the implant is connected to the electrode lead, the method comprising the following steps:

transmitting an electromagnetic query signal using the electrical conductor to be read and the communication antenna, wherein the query signal is configured such that the communication antenna and the electrical conductor together are operated as a bipolar antenna, wherein the query signal is produced by the control device connected to the electrical conductor to be read and the communication antenna;

activating the RFID label by receiving the query signal by means of the inlay antenna of the RFID label and forwarding the received query signal to the RFID chip;

processing the received query signal using the RFID chip (200), producing a corresponding electromagnetic reply signal using the RFID chip, and transmitting the reply signal by means of the inlay antenna of the RFID label;

receiving the reply signal using the bipolar antenna comprising the communication antenna and the electrical conductor of the electrode lead to be read; and, processing the received reply signal forwarded to the control device in the control device.

The inventive method permits, in a simple and cost-effective manner, detection of the electrical conductor(s) of an electrode lead or retrieval of information about the electrode lead. Examples of such information are provided above. As already stated in the foregoing, the inventive method may be executed with a very small amount of energy due to the coupling of the communication antenna with the electrical conductor of the electrode lead.

In one preferred exemplary embodiment, the query signal may be produced by the control device at regular and/or prespecifiable time intervals and/or after the occurrence of a prespecified event. Such events may be, e.g.: the attachment of an electrode lead or the exchange of an electrode lead, an annual/monthly inventory of the implant via the remote query of a central patient data center, a defined change in an electrical property of an electrode lead (e.g., due to a change in impedance).

In another preferred exemplary embodiment, the query signal for the RFID label may be produced by the control device at regular and/or prespecifiable time intervals and, following successful detection of a new RFID label, may trigger an additional activity. Such an activity may preferably be activation of a detection process that determines the socket of the implant to which an electrode lead is attached.

If a plurality of electrode leads are attached to the implant, the information for each electrode lead must be allocated to the socket of the implant occupied by that electrode lead. This is attained in a particularly simple manner in that, when two or more than two electrode leads are connected to the implant, wherein of these electrode leads one electrode lead is newly attached to the implant, i.e., was just attached to the implant, the method for identifying all attached electrode leads is executed successively for each electrode lead. This means that the query method is executed both for the electrode leads that had already been attached and for the newly attached electrode lead. Then the reply signal of each electrode lead is compared to the information on electrode leads already stored in a memory device of the implant. Based on the result of the comparison, the information from the RFID chip of the RFID label about the newly attached electrode lead is allocated to the socket of the implant connected to the new electrode lead.

At least the above object(s) is furthermore attained using an implant having a socket for connecting to the plug of an electrode lead described in the foregoing and having a housing, wherein arranged in the housing is a control device that is connected to a communication antenna. According to the present invention, it is provided that the control device is set up for processing an electromagnetic reply signal that is received and forwarded to the control device by a bipolar antenna, comprising the communication antenna and the electrical conductor of the electrode lead, wherein the plug of the electrode lead is inserted into the socket so that the electrical conductor is electrically connected to the control device. Such an active implant enables simple and cost-effective identification of the electrode leads attached to the implant and retrieval of the information relating to the electrode lead.

It is particularly preferred that the control device is also set up for producing an electromagnetic query signal that is likewise sent using a bipolar antenna comprising the communication antenna and the electrical conductor of the electrode lead, wherein the plug of this electrode lead is inserted into the socket so that the electrical conductor is electrically connected to the control device.

In order to be able to address the individual conductors of the electrode lead individually, it is advantageous that the socket has a plurality of connectors for connecting to the plurality of electrical conductors of one electrode lead or of a plurality of electrode leads and that a transmitter and/or receiver unit of the control device is provided that is connected via a multiplexer to the plurality of connectors.

As has already been depicted in the foregoing, it is advantageous that the control device is set up such that it produces the query signal at regular and/or prespecifiable time intervals and/or following the occurrence of a predetermined event.

In one refinement of the present invention, the implant also has a detection unit that detects that an electrode lead is attached to the implant. The detection unit measures the impedance of each of the connectors of the socket for the electrode leads on the implant, wherein a sharp increase in the impedance at a connector indicates successful contacting of an electrode lead to the socket of the implant containing this connector. The detection unit is set up for generating a trigger signal that is produced when the detection unit detects a newly connected electrode lead. The trigger signal is transmitted to a signal input of the control device, which then initiates the query process of the RFID label.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other aspects, features and advantages of at least one embodiment of the present invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the present invention. This description is not to be taken in a limiting sense, but is made merely for the purpose of describing the general principles of the present invention. The scope of the present invention should be determined with reference to the claims.

Figure 1:
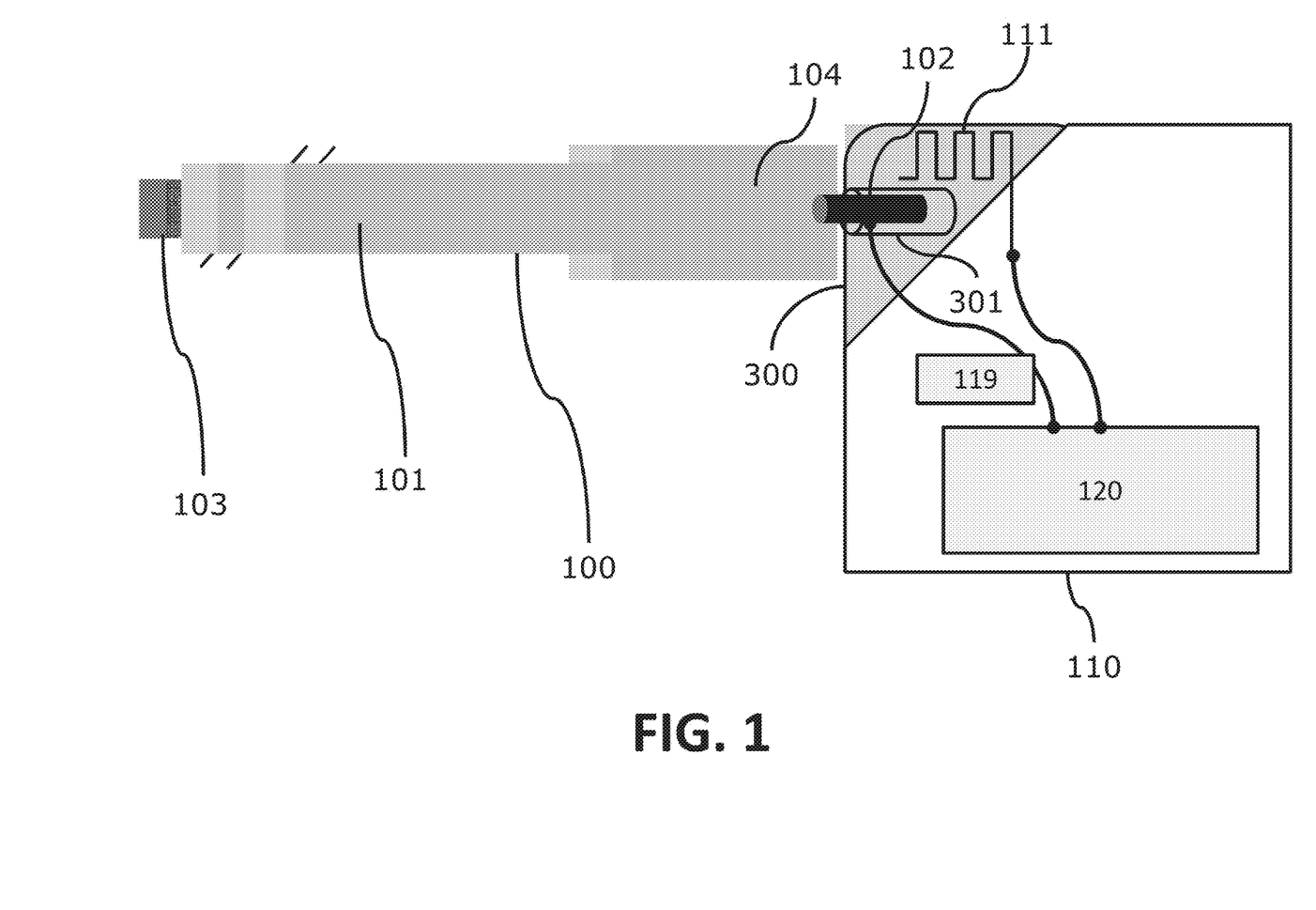
FIG. 1 is a perspective elevation, from the side, of an exemplary embodiment of an inventive electrode lead, connected to an inventive implant.

FIG. 1 depicts an exemplary embodiment of an inventive electrode lead 100 having an electrical conductor 101. Alternatively, it is also possible for a plurality of electrical conductors 101 to be provided. Arranged at the distal end of the electrode lead 100 is an electrode tip 103 that produces the electrical contact to the surroundings, for instance to the tissue of the patient. The electrode tip may be embodied as a stimulating electrode, measuring electrode, or recording electrode. Arranged at the proximal end of the electrode lead 100 is a plug 102 that is inserted into a socket 301 of an active implant 110, which socket is disposed on a header block 300 of the implant 110. Frequently, the implant 110 has a plurality of sockets 301, and the plug 102 of an electrode lead 100 is inserted into each of them. The active implant 110 may be embodied, for instance, as a cardiac pacemaker or defibrillator. Due to the plug 102, there is a mechanical and electrical connection between the electrode lead 100 and the active implant 110. Via corresponding connectors of the plug 102 and socket 301 there is, in particular, an electrically conducting connection between the electrical conductor 101 of the electrode lead 100 and the interior electrical components of the implant 110, for instance a control device 120.

Figure 2:
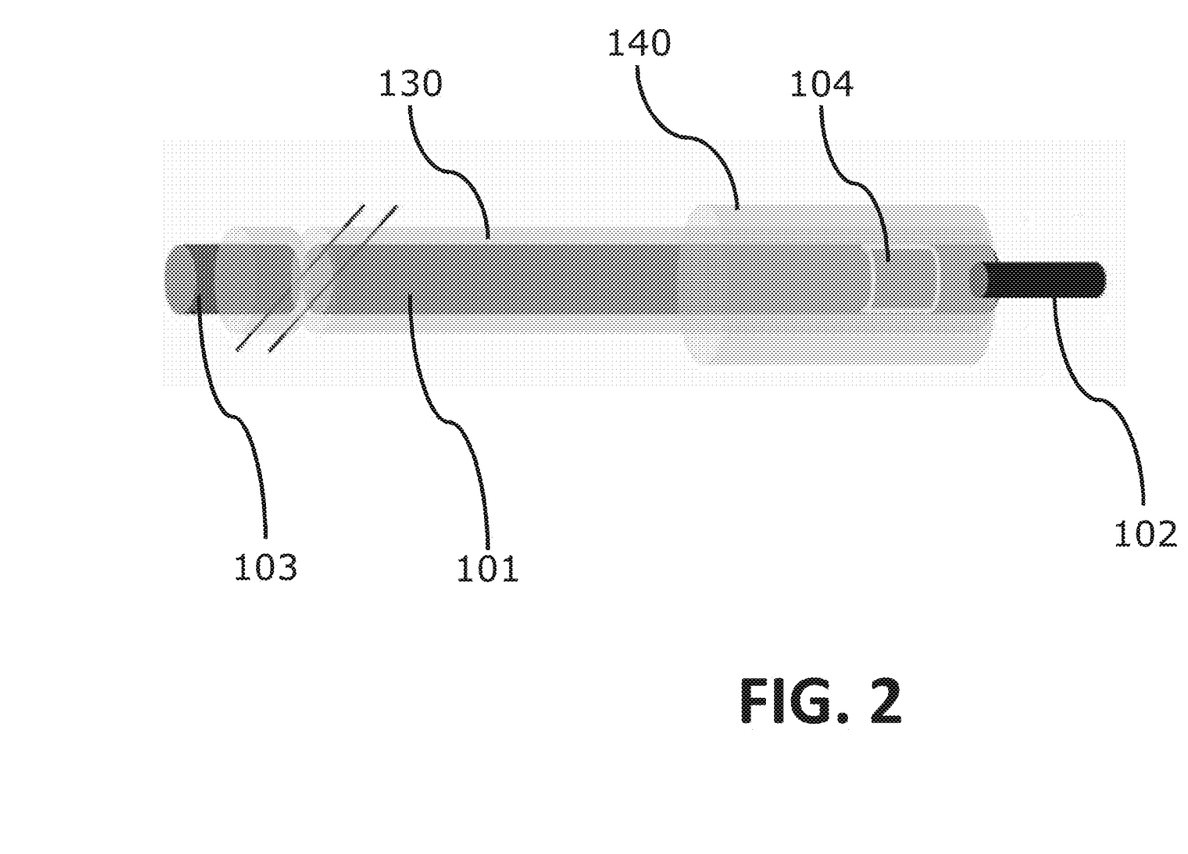
FIG. 2 is another perspective elevation, from the side, of the electrode lead according to FIG. 1.

A passive RFID label 104 is arranged between an insulating tube 130, embodied, for instance, as a silicone tube, and an insulating sleeve 140 provided at the proximal end of the electrode lead 100 in the vicinity of the plug 102. The insulating sleeve 140 may be embodied as a separate additional part that can be placed over the insulating tube 130. The insulating sleeve 140, which comprises, for instance, a liquid crystal polymer (LCP), silicone, a ceramic, and/or glass, surrounds the insulating tube 130 such that the RFID label 104 is hermetically sealed against the surroundings.

Alternatively, the RFID label 104 may also be integrated in the plug 102. This has the advantage that, after the plug 102 has been inserted into the socket 301 of the implant 110, the RFID label 104 is arranged inside the stiff header block 300 of the implant 110 in which the socket 301 is provided, and thus is protected against high mechanical loads (e.g., bending, abrasive wear). Another advantage of this is that if the RFID 104 is arranged physically close to the implant 110, there are lower losses during retrieval and thus a lower RF load for the patient.

Figure 4:
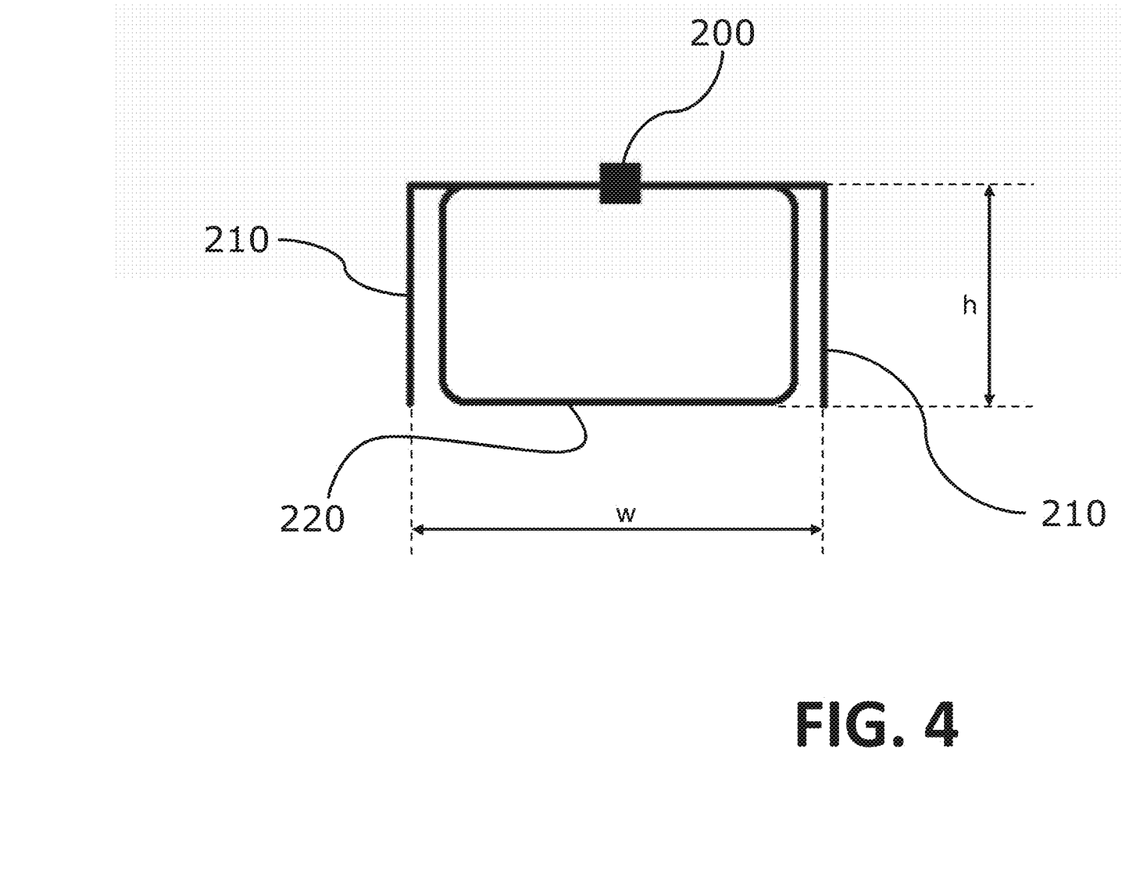
FIG. 4 depicts an RFID label of the electrode lead according to FIG. 1.

FIG. 4 depicts one exemplary embodiment of an RFID label 104. It is embodied, for instance, as a passive RFID label 104 approx. 1 cm$^2$ in size (dimensions, for instance: width w=16 mm, height h=6 mm, thickness d<0.1 mm) and has an RFID chip 200 and an inductor 220 that surrounds the RFID chip 200 in a loop shape and that is for adjusting the impedance. Furthermore, an inlay antenna 210 is provided that has two segments in this exemplary embodiment. The inlay antenna 210 may be produced, for instance, by means of metallizing a plastic film, preferably with gold or platinum, wherein the metallization may also be added to the inside of the insulating sleeve 140, for instance, a ceramic or glass sleeve. In the RFID label 104, the complex conjugated of the impedance of the RFID chip 200 equals the impedance of the RFID inlay, wherein the RFID inlay comprises an inlay antenna 210 and a loop 220 for adjusting the impedance of the RFID inlay.

A chip for the frequency range between 840 MHz and 960 MHz may be used for the RFID chip 200, for example. Moreover, a memory capacity of 512 free text and 240 bits for storing the electronic product code (EPC) may be provided. The memory of the RFID chip 200 may be read and/or written both during production at the factory and while the inventive method for identifying an electrode lead 100 is being executed. Information for identifying the electrode lead 100 and for its use may be included in the memory of the RFID chip 200. Such information may comprise: manufacturer, type of electrode lead, serial number, date of manufacture, authorized regions, authorized conditions, date of implantation, implantation compatibility, MRI compatibility, and the like. The memory of the RFID chip 200 may furthermore include safety mechanisms and safety information that safeguard or identify the integrity (for instance, if some of the data are lost) and/or the authenticity (for instance, during manipulation) of the stored information.

As already explained in the foregoing, the implant 110 includes a control device 120 that is hermetically sealed against the outside and that is connected to the connector or connectors in the socket 301 for the electrode lead 100. Once an electrode lead 100 has been inserted into a corresponding socket 301 in a header block 300 of the implant (110) (see FIG. 3), there is an electrically conducting connection between the control device 120 and the one electrical conductor 101 or the plurality of electrical conductors 101 of the electrode lead 100. These occur using vias 122 into the interior of the encapsulated implant 110.

Figure 3:
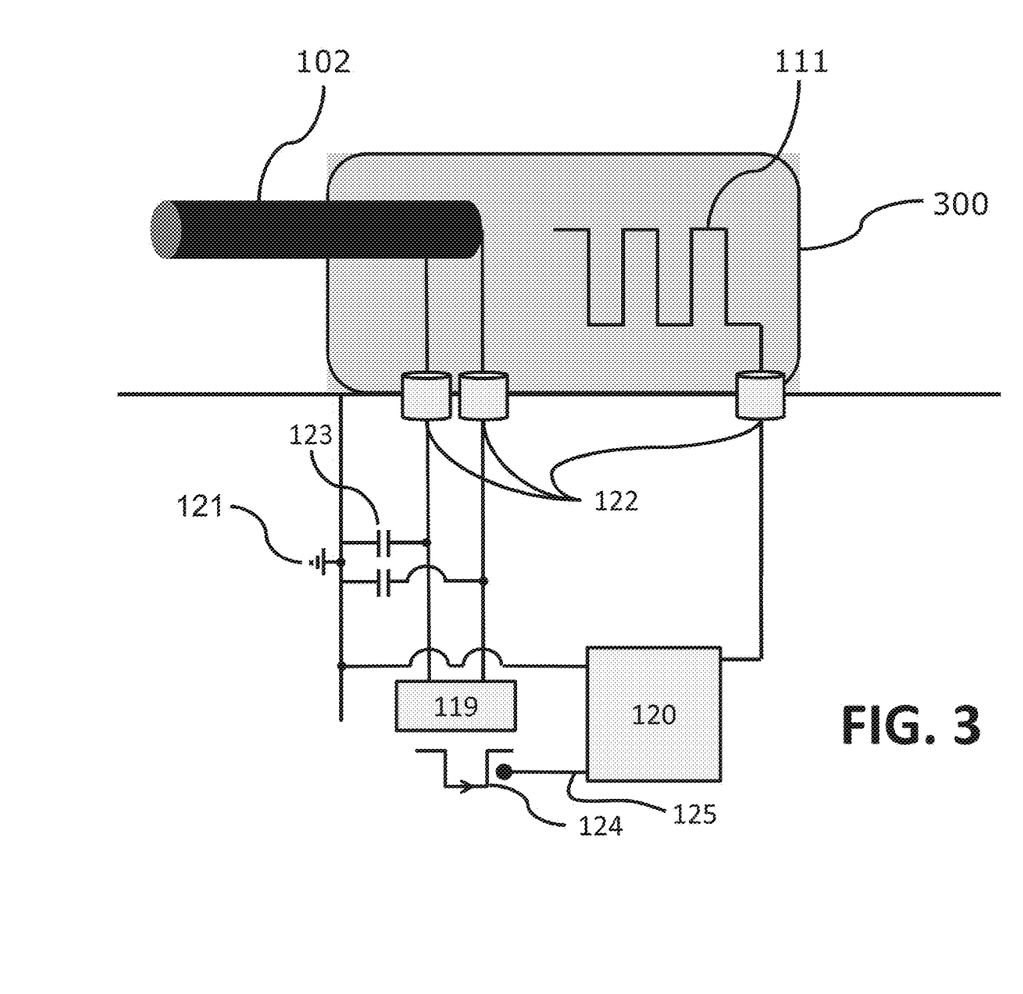
FIG. 3 is a diagram of a circuit for the implant according to FIG. 1.

Furthermore, a communication antenna 111 is provided in the header block area 300 of the implant 110. The communication antenna 111 may also be used as the antenna for transmitting data to an external receiver that, e.g., transmits data to a patient data center or permits remote querying and/or programming of the implant 110. The communication antenna 111 is connected in an electrically conducting manner to the control device 120 via a feedthrough 122. The communication antenna 111 preferably has a best possible adjustment for the frequency range provided for communication, via the inlay antenna 210, with the RFID chip 200 embedded in the RFID label 104. Moreover, the communication antenna 111 preferably has isotropic directivity. For antennas 111 that have non-isotropic directivity for the purpose of communication between the implant 110 and an external device, the proximal area of the inserted electrode lead 100 is preferably in the preferred radiating area of the antenna 111.

The active implant 110 furthermore has a filter unit against electromagnetic interference, in order, for instance, to prevent mobile telephone signals from penetrating into the interior of the encapsulated housing of the implant 110. The filter unit short-circuits high-frequency signals (frequency>1 kHz) to the electrical ground 121. High-capacity capacitors 123 switched in parallel, for example, are used for this.

According to the present invention, the communication antenna 111 is used as a bipolar antenna, wherein all available electrical conductors 101 of all electrode leads 100 and the housing of the implant 110 are used as the antipole of the communication antenna 111. If a detection unit 119 of the implant 110 detects that an electrode lead 100 has just been connected to the implant 110, the detection unit 119 generates a trigger signal 124 that is conducted to the signal input 125 of the control device 120. One possible way to detect whether the plug 102 of an electrode lead 100 has been attached to a certain socket 301 of the implant 110 is to measure, at regular intervals using the detection unit 119, the impedance of each of the connectors for the socket 301 for the electrode leads 100 on the implant 110, wherein a sharp increase in the impedance at a connector of a socket 301 indicates successful contacting of an electrode lead 100 to this socket 301 of the implant 110. If the control device 120 detects the trigger signal 124 at its signal input 125, the control unit 120 generates a high-frequency query signal in the appropriate frequency range (for instance, 860 MHz) and emits it to the electrical conductor 101 of the electrode lead 100 and communication antenna 111, which are operated together as a bipolar antenna. If two or more than two electrode leads 100 are attached to the implant 110, the query signal is transmitted simultaneously to all contacted electrical conductors 101 of all attached electrode leads 100.

For operating the electrical conductors 101 of the electrode leads 100 attached to the implant 110 and the communication antenna 111 as a bipolar antenna, it is advantageous when the path difference of the phases between the electrode conductors 101 of the electrode lead 100 and the communication antenna 111 is about 180°.

The query signal couples into the inlay antenna 210 of the RFID label 104 of the specific electrode lead 100 and activates the associated RFID chip 200. The reply signal of the RFID label 104 of the specific electrode lead 100 that is generated by this and that is transmitted by the associated inlay antenna 210 is received by the bipolar antenna, comprising the communication antenna 111 and the electrical conductor 101 of the electrode lead 100, and is forwarded to the control device 120. The latter further processes the reply signal. Due to the close physical proximity of the hermetically encapsulated RFID label 104, the electrical conductor 101, and the communication antenna 111, it is possible to obtain satisfactory electromagnetic coupling, even when the adjustment is not optimal. Electrical conductors 101 that are disposed in the immediate vicinity of the header block area 300 of the implant 110 without being contacted with the active implant 110 are either not read or are read with only a very low RSSI (received signal strength indicator). The RSSI is determined by the control unit 120, e.g., by determining the quotients of the received amplitudes and transmitted amplitudes. As soon as the electrical conductor 101 of an electrode lead 100 is connected to the antipole of the control device 120, the information from the RFID chip 200 in question may be read or the RSSI value of the signal increases sharply.

The individual electrode leads 100 are assigned to the sockets 301 of the implant 110 using a logic within the implant 110, said logic being described in the following. The electrode lead 100, detected using impedance measurement and just attached to a specific socket 301 of the implant 110, is identified using a comparison to the last triggered read process. For this, a memory device of the implant 110 compares the stored information (e.g., electrode type and connector to the implant 110) for the electrode leads 100 from previous query methods to the received reply signals of the electrode leads 100, and, based on the results of this comparison, assigns the information about the just attached electrode lead 100 to the appropriate sockets 301 of the implant 110.

With the inventive solution, specific information of the electrical conductor 101 of an electrode lead 100 may be retrieved without influencing the therapeutic path through galvanic coupling. The electrical conductor 101 of an electrode lead 100 acts as the antipole, so that the information is not retrieved until after contacting. Surprisingly, due to the bipolar antenna formed on the active implant 110 from the electrical conductor 101 and communication antenna 111, the power required for retrieving the information is clearly reduced compared to a query in which only the antenna 111 of the implant 110 is used. It is not necessary to circumvent the EMI filter device to execute the retrieval process.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this invention, which is to be given the full breadth thereof.

Additionally, the disclosure of a range of values is a disclosure of every numerical value within that range, including the end points.

REFERENCE LIST

100 Electrode lead
101 Electrical conductor
102 Plug
103 Electrode tip
104 RFID label
110 Implant
111 Communication antenna
119 Detection unit
120 Control device
121 Ground
122 Execution
123 Capacitor for the EMI filter unit
124 Trigger signal
125 Signal input for the control device 120
130 Insulating tube
140 Insulating sleeve
200 RFID chip
210 Inlay antenna
220 Inductance for adjusting impedance
300 Header block area of the implant 110
301 Socket

I claim:

1. A method for identifying an electrode lead by means of an implant, the electrode lead comprising:
   a plug for connecting to the implant,
   at least one electrical conductor,
   an insulating tube that insulates the at least one electrical conductor, and
   a hermetically sealed passive RFID label embedded:
      in the insulating tube, and/or
      in the plug, or
      in an insulating body of a separate additional part that is connectable to the insulating tube or the plug, preferably in a positive fit,
   wherein the RFID label has an RFID chip and an inlay antenna connected in an electrically conducting manner to the RFID chip,
   wherein the inlay antenna is electromagnetically coupled to the at least one electrical conductor and the communication antenna,
   wherein the implant has a control device and an communication antenna connected to the control device, and
   wherein the implant is connected to the electrode lead,
   the method comprising the following steps:
      transmitting an electromagnetic query signal using the electrical conductor to be read and the communication antenna, wherein the query signal is configured such that the communication antenna and the electrical conductor together are operated as a bipolar antenna, wherein the query signal is produced by the control device connected to the electrical conductor to be read and the communication antenna;
      activating the RFID label by receiving the query signal by means of the inlay antenna of the RFID label and forwarding the received query signal to the RFID chip;
      processing the received query signal using the RFID chip, producing a corresponding electromagnetic reply signal using the RFID chip, and transmitting the reply signal by means of the inlay antenna of the RFID label;
      receiving the reply signal using the bipolar antenna comprising the communication antenna and the electrical conductor of the electrode lead to be read; and,
      processing the received reply signal forwarded to the control device in the control device.

2. The method according to claim 1, wherein the query signal is produced by the control device at regular and/or prespecifiable time intervals and/or after the occurrence of a prespecified event, after an electrode lead has been attached to the implant.

3. The method according to claim 1, wherein if two or more than two electrode leads are attached to the implant, wherein of these electrode leads one electrode lead is newly attached to the implant, the identification method for all attached electrode leads is executed successively for all attached electrode leads and in that each reply signal is compared to the information on electrode leads already stored in a memory device of the implant and, based on the result of the comparison, the information of the newly attached electrode lead is allocated to the socket of the implant connected to the new electrode lead.

* * * * *